(12) United States Patent
Kawazoe et al.

(10) Patent No.: US 6,484,570 B2
(45) Date of Patent: Nov. 26, 2002

(54) IMPRESSION FORMING MECHANISM AND HARDNESS TESTING APPARATUS

(75) Inventors: Masaru Kawazoe, Zama (JP); Takeaki Iida, Zama (JP); Yuichi Minami, Zama (JP); Mitsuru Oda, Zama (JP)

(73) Assignee: Akashi Corporation, Kanagawa-ken (JP)

( * ) Notice: Subject to any disclaimer, the term of this patent is extended or adjusted under 35 U.S.C. 154(b) by 0 days.

(21) Appl. No.: 09/998,315

(22) Filed: Dec. 3, 2001

(65) Prior Publication Data

US 2002/0033044 A1 Mar. 21, 2002

Related U.S. Application Data

(62) Division of application No. 09/292,937, filed on Apr. 16, 1999, now Pat. No. 6,336,359.

(30) Foreign Application Priority Data

Feb. 17, 1999 (JP) ............................................. 11-38913
Feb. 17, 1999 (JP) ............................................. 11-38914

(51) Int. Cl.$^7$ ................................................. G01N 3/42
(52) U.S. Cl. .......................................................... 73/82
(58) Field of Search ....................................... 73/78–82

(56) References Cited

U.S. PATENT DOCUMENTS

| 3,693,417 A | * | 9/1972 | Fritz et al. ...................... 73/81 |
| 4,444,045 A | | 4/1984 | Ernst |
| 4,699,000 A | * | 10/1987 | Lashmore et al. .............. 73/81 |
| 4,899,577 A | | 2/1990 | Fischer |
| 5,067,346 A | | 11/1991 | Field |
| 5,305,633 A | | 4/1994 | Weissenbacher et al. |
| 5,616,857 A | | 4/1997 | Merck, Jr. et al. |

FOREIGN PATENT DOCUMENTS

| JP | A-56-166447 | 12/1981 |
| JP | A-63-168534 | 7/1988 |
| JP | A-4-42036 | 2/1992 |
| JP | U-4-85256 | 7/1992 |

* cited by examiner

*Primary Examiner*—Robert Raevis
(74) *Attorney, Agent, or Firm*—Oliff & Berridge, PLC

(57) ABSTRACT

An impression forming mechanism comprises; an arm with an indentor for forming an impression on a surface of a sample, and an arm operating part for operating the arm in order to apply a force to the sample, wherein the arm operating part is disposed below the arm.

16 Claims, 7 Drawing Sheets

IMPRESSION FORMING MECHANISM AND HARDNESS TESTING APPARATUS

This is a Division of application Ser. No. 09/292,937 filed Apr. 16, 1999, now issued as U.S. Pat. No. 6,336,359. The entire disclosure of the prior application is hereby incorporated by reference herein in its entirety.

BACKGROUND OF THE INVENTION

1. Field of the Invention

The present invention relates to an impression forming mechanism which is used for a testing apparatus for evaluating material characteristics of a sample by applying force to the surface of the sample with an indentor in order to form an impression thereon and a hardness testing apparatus comprising the above-described the impression forming mechanism.

2. Description of the Related Art

There is a hardness testing apparatus for evaluating material characteristics of a sample by applying force to the surface of the sample with an indentor in order to form an impression thereon.

FIG. 7 shows a force applying mechanism which is used for the above-described hardness testing apparatus.

In FIG. 7, a hardness testing apparatus 200 which is a so-called Rockwell hardness testing apparatus, comprises an impression forming mechanism 210 comprising weights 201, a loading arm 202, a cam 203, a force shaft 204, an indentor shaft 205, an indentor 206, or the like.

In the impression forming mechanism 210, the weights 201 having a predetermined weight are hung from an end of the loading arm 202. The end of the loading arm 202 moves down by the rotation of the cam 203. A predetermined force is applied to the force shaft 204. The force applied to the force shaft 204 is transmitted to the indentor 206 through the indentor shaft 205. An impression is formed on a sample mounted on a sample mounting member 207 by moving down the indentor 206.

A force applying control of the above force applying mechanism is carried out by hanging the weights 201 having a predetermined weight from the loading arm 202.

Further, a force applying control, for example, disclosed in the U.S. Pat. No. 5,616,857, is known. A force applied to a sample is measured by a load cell disposed on the axis which is the same as that of an indentor. The force applying control is carried out so that an actual force measured by the load cell will approximate to a set force on the basis of result of comparing the actual force data with the set force data.

Recently, it is necessary that measuring instruments and apparatus including the above-described hardness test apparatus should be small.

However, in the above-described hardness test apparatus, the loading arm 202 is disposed apart from the indentor 206. Because the principal part of the impression forming mechanism is disposed in the position which is higher than that of the indentor 206, there is a problem that the hardness testing apparatus is so difficult to be small in the height direction.

Further, in the force applying control carried out by using weights, there is a problem that it cannot be confirmed whether the force having a set value is applied to a sample while an impression is formed on the surface of the sample.

In the case of the force applying control carried out by using the load cell, although the force for forming an impression can be set to the set value approximately, the load cell is strained by applying the force thereto. As a result, there is a problem that a measurement error is caused in proportion to an amount of the strain. Because the load cell is precious relatively, a force applying mechanism which can carry out the force applying control cheaper and more precisely is required.

SUMMARY OF THE INVENTION

In order to solve the above-described problems, an object of the present invention is to provide an impression forming mechanism which can easily make a testing apparatus be small in a height direction and a hardness testing apparatus which is made to be small.

Another object of the present invention is to provide an impression forming mechanism which can carry out a force applying control cheaper and more precisely and a hardness testing apparatus which can carry out a force applying control cheaper and more precisely.

That is, in accordance with one aspect of the present invention, the impression forming mechanism which is used for a testing apparatus for measuring material characteristics of a sample by forming an impression with an indentor on a surface of the sample, comprises; a body part, an arm which is supported by the body part so as to be movable rotationally, for attaching the indentor to a free end portion thereof, and an arm rotating force applying part for applying a force to the arm in order to move a free end side of the arm rotationally and in order to apply a pressing force for forming an impression on the surface of the sample, wherein the arm rotating force applying part is attached to the body part below the arm.

According to the present invention, because the arm rotating force applying part for moving the free end side of the arm rotationally is disposed to the body part below the arm and the indentor is attached to the arm directly, the structure of the parts disposed above the indentor can be more simple than that of the mechanism in which the arm is disposed apart from the indentor and in which a part for operating the arm is disposed between them, according to the earlier development. The impression forming mechanism can make a testing apparatus be small in a height direction by attaching the impression forming mechanism to a hardness testing apparatus.

For example, the testing apparatus for measuring material characteristics of a sample by forming an impression with an indentor on a surface of the sample is a hardness testing apparatus for measuring a hardness of a sample, a testing apparatus for measuring an electric resistance of a sample when an impression is formed on the surface of the sample or the like. However, the testing apparatus is not limited to them. The all of apparatuses having an impression forming mechanism are included.

For example, the arm rotating force applying part is a motor for moving the arm rotationally by moving up and down a ball screw, a hydraulic device or a pneumatic one for moving the arm rotationally by moving up and down a piston, or the like. However, the arm rotating force applying part is not limited to them. Any device which can move the arm rotationally, may be used.

The impression forming mechanism may further comprise a rotating force transmitting member for transmitting the force generated by the arm rotating force applying part to the arm as a rotating force.

According to the present invention, in particular, the force generated by the arm rotating force applying part can be transmitted to the arm as a rotating force by the rotating force transmitting member completely.

For example, the arm rotating force applying part may be a rigid body or an elastic body like a plate spring.

The body part may contain a part of the arm rotating force applying part.

Because a part of the arm rotating force applying part is contained in the body part, the impression forming mechanism can be small.

The impression forming mechanism may further comprise an electric operating member, wherein the arm rotating force applying part applies a rotating force to the arm by operating the electric operating member.

Because the electric operating member applies the rotating force to the arm, the rotational movement of the arm can be controlled more precisely than the movement of the arm, which is carried out by weights and cam mechanism according to the earlier development.

In accordance with another aspect of the present invention, the impression forming mechanism which is used for a testing apparatus for measuring material characteristics of a sample by forming an impression with an indentor on a surface of the sample, comprises; a force applying part for applying a force in order to apply a pressing force for forming an impression on the surface of the sample to the indentor, a force transmitting member for transmitting the force applied by the force applying part to the indentor, which is deformed elastically by the force applied by the force applying part, a deformation measuring unit for measuring an amount of an elastic deformation of the force transmitting member by setting a predetermined reference position of a predetermined part thereof to a reference point, and a force applying control unit for controlling the force applied by the force applying part on the basis of the amount of the elastic deformation of the force transmitting member, which is measured by the deformation measuring unit.

According to the present invention, the force applied by the force applying part is transmitted to the indentor by the force transmitting member. At the same time, the force transmitting member is deformed elastically by the force. An amount of an elastic deformation of the force transmitting member is measured by the deformation measuring unit by setting the predetermined reference position of the predetermined part thereof to a reference point. Because the control of applying the force by the force applying part is carried out by the force applying control unit on the basis of the amount of the measured elastic deformation, it is possible not only that the force (load) for forming the impression becomes the set value approximately but also that the force applying control is carried out without the load cell. As a result, the force applying control can be carried out cheaper.

Further, because the loading arm is used and the force control is carried out on the basis of the displacement of the force transmitting member, it is not necessary that the compensating control which must be carried out when the force control is carried out by using the load cell because of the structural defect of the load cell, in which an amount of an indentation (that is, a hardness of a sample) includes an amount of a strain of the load cell, is carried out. As a result, an amount of an indentation of the indentor can be measured precisely. The above method is effective, in particular when an amount of an indentation of the indentor is measured dynamically and a hardness of a sample is calculated.

For example, the testing apparatus for measuring material characteristics of a sample by forming an impression with an indentor on a surface of the sample is a hardness testing apparatus for measuring a hardness of a sample, a testing apparatus for measuring an electric resistance of a sample when an impression is formed on the surface of the sample or the like. However, the testing apparatus is not limited to them. The all of apparatuses having an impression forming mechanism are included.

For example, the force applying part is a motor for moving the arm rotationally by moving up and down a ball screw, a hydraulic device or a pneumatic one for moving the arm rotationally by moving up and down a piston, or the like. However, the force applying part is not limited to them. Any device which can move the arm rotationally, may be used.

For example, the force applying part is an elastic body like a spring, a rubber or the like.

Although a linear scale, a capacitance displacement transducer, an LVDT (a linear variable differential transformer), an electric micrometer or the like is used in the deformation measuring unit, the present invention is not limited to them. Any unit which can measure an amount of the elastic deformation of the force applying part, may be used.

In the force applying control which is carried out on the basis of the amount of the elastic deformation of the force transmitting member, which is measured by the deformation measuring unit, for example, an amount of the measured elastic deformation is compared with a reference amount of the elastic deformation, which is previously set, and then the control is carried out on the basis of result of the above comparison, or the like.

The predetermined reference position may be a position in an initial condition in which the force transmitting member is not deformed elastically, or may be an optional position in a condition in which the force transmitting member is deformed elastically.

The control of the force applied by the force applying part may be a closed loop control.

According to the present invention, in particular, because the control of the force applied by the force applying part is carried out in a closed loop, the force applying control is always carried out. As a result, the force for forming the impression can become the set force more approximately.

The force transmitting member may be a spring body.

According to the present invention, because the force transmitting member is a spring body, the spring body and the deformation measuring unit can obtain the effect which is the same as the load cell. As a result, the force control can be carried out precisely. The impression forming mechanism is manufactured cheaper.

The spring body is a plate spring, a rod spring, a helical spring or the like.

In accordance with another aspect of the present invention, the hardness testing apparatus comprises; a body part, an arm which is supported by the body part so as to be movable rotationally, for attaching an indentor to a free end portion thereof, an arm rotating force applying part for applying a force to the arm in order to move a free end side of the arm rotationally and in order to apply a pressing force for forming an impression on a surface of a sample, and a hardness calculating mechanism part for measuring a shape of an impression formed on the surface of the sample, and for calculating a hardness of the sample on the basis of a result of measuring the shape of the impression, wherein the arm rotating force applying part is attached to the body part below the arm.

According to the present invention, the hardness testing apparatus can be small by applying the above impression forming mechanism.

For example, the hardness calculating mechanism part may be a device for calculating a hardness of the sample on the basis of the depth of the impression, or a device for calculating a hardness of the sample on the basis of the size of the indentation formed by the indentor. However, the hardness calculating mechanism part is not limited to them. Any hardness calculating mechanism part which can measure the hardness of the sample, may be used.

The hardness calculating mechanism part is, for example, a Rockwell hardness testing apparatus, a Vickers hardness testing apparatus or the like.

The hardness testing apparatus may further comprise a rotating force transmitting member for transmitting the force generated by the arm rotating force applying part to the arm as a rotating force.

The body part may contain a part of the arm rotating force applying part.

The hardness testing apparatus may further comprise an electric operating member, wherein the arm rotating force applying part applies a rotating force to the arm by operating the electric operating member.

In accordance with another aspect of the present invention, the hardness testing apparatus comprises; a force applying part for applying a force in order to apply a pressing force for forming an impression on a surface of a sample to an indentor, a force transmitting member for transmitting the force applied by the force applying part to the indentor, which is deformed elastically by the force applied by the force applying part, a deformation measuring unit for measuring an amount of an elastic deformation of the force transmitting member by setting a predetermined reference position of a predetermined part thereof to a reference point, a force applying control unit for controlling the force applied by the force applying part on the basis of the amount of the elastic deformation of the force transmitting member, which is measured by the deformation measuring unit, and a hardness calculating mechanism part for measuring a shape of the impression formed on the surface of the sample, and for calculating a hardness of the sample on the basis of a result of measuring the shape of the impression.

According to the present invention, it is possible to provide the precise and cheap hardness testing apparatus by comprising the above impression forming mechanism.

For example, the hardness calculating mechanism part may be a device for calculating a hardness of the sample on the basis of the depth of the impression, or a device for calculating a hardness of the sample on the basis of the size of the indentation formed by the indentor. However, the hardness calculating mechanism part is not limited to them. Any hardness calculating mechanism part which can measure the hardness of the sample, may be used.

The hardness calculating mechanism part is, for example, a Rockwell hardness testing apparatus, a Vickers hardness testing apparatus or the like.

The control of the force applied by the force applying part may be a closed loop control.

The force transmitting member may be a spring body.

In accordance with another aspect of the present invention, the impression forming mechanism comprises; an arm with an indentor for forming an impression on a surface of a sample, and an arm operating part for operating the arm in order to apply a force to the sample, wherein the arm operating part is disposed below the arm.

The arm operating part may apply a rotational force to the arm in order to move the arm rotationally around a fixed end of the arm.

The impression forming mechanism may further comprise a motor for operating the arm operating part.

In accordance with another aspect of the present invention, the impression forming mechanism comprises; an elastic body f or storing a force for forming an impression on a surface of a sample, a deformation measuring member for measuring an amount of a deformation of the elastic body, and a force control unit for controlling the force stored in the elastic body on the basis of measuring the amount of the deformation of the elastic body.

The force control unit may comprises a closed loop system for controlling the force stored in the elastic body in a closed loop.

BRIEF DESCRIPTION OF THE DRAWINGS

The present invention will become more fully understood from the detailed description given hereinbelow and the accompanying drawings which are given by way of illustration only, and thus are not intended as a definition of the limits of the present invention, and wherein.

PREFERRED EMBODIMENTS OF THE INVENTION

Hereinafter, an impression forming mechanism and a hardness testing apparatus according to the first embodiment of the present invention will be explained in detail with reference to the FIGS. 1 to 3.

Figure 1:
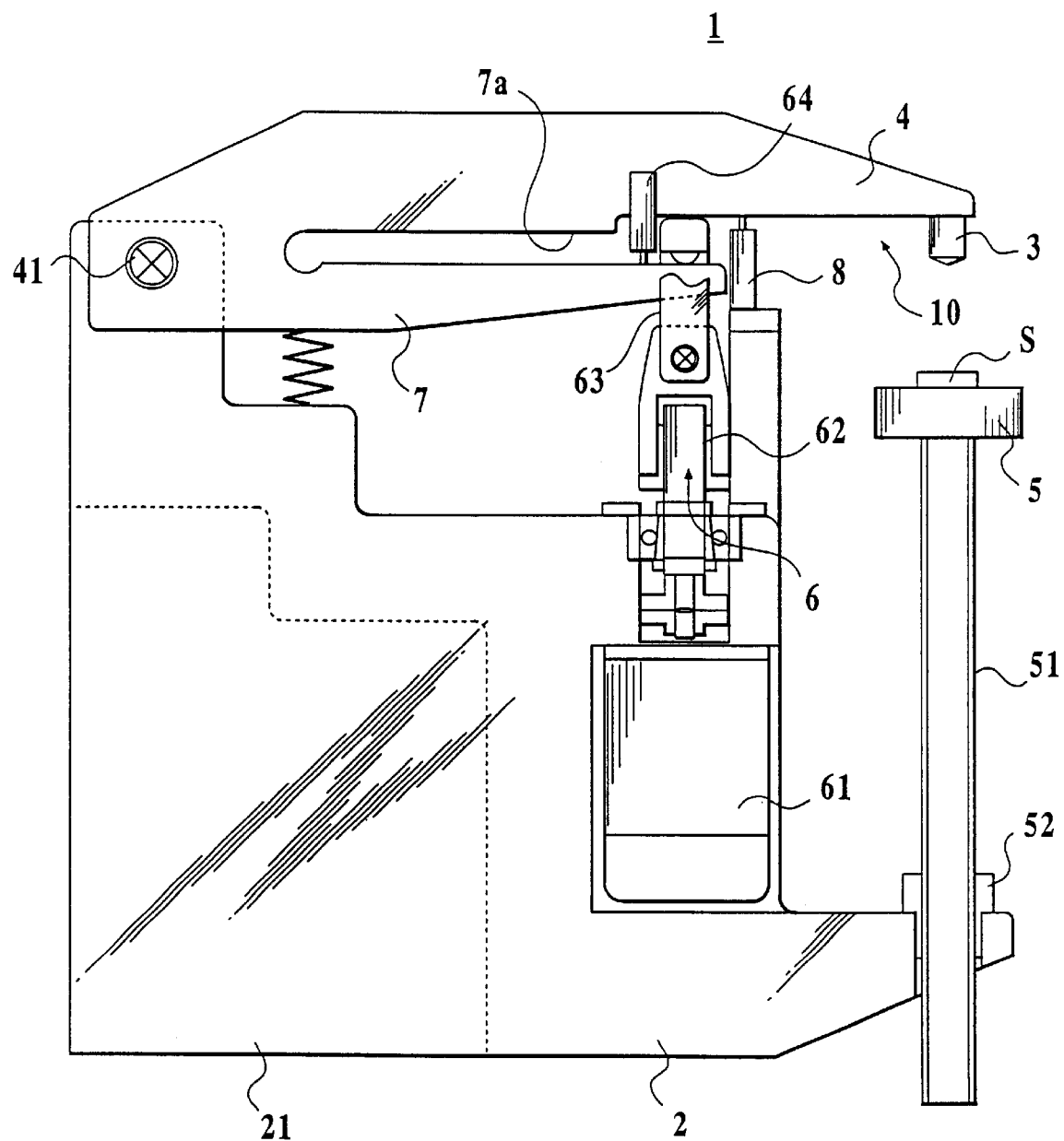
FIG. 1 is a side view showing a principal structure of a hardness testing apparatus according to the first embodiment of the present invention.

FIG. 1 is a side view showing a principal structure of a hardness testing apparatus according to the first embodiment of the present invention. FIG. 2 is a block diagram showing a principal structure of a loading arm operation controlling unit according to the first embodiment of the present invention. FIG. 3 is a block diagram showing a principal structure of a hardness calculating mechanism part according to the first embodiment of the present invention.

The hardness testing apparatus 1 shown in FIG. 1 comprises an impression forming mechanism 10 comprising a testing apparatus body 2, a loading arm 4 which is supported by the testing apparatus body 2 so as to be movable rotationally and which has an indentor 3 attached to the free end thereof, a sample mounting member 5 for mounting a sample S, which is attached to the testing apparatus body 2 below the indentor 3, a loading arm operating part 6 arranged below the loading arm 4, which applies force (load) for pressing a surface of the sample S in order to form an impression thereon by moving the free end side of the loading arm 4 rotationally, a plate spring 7 for transmitting force generated by operating the loading arm operating part 6 to the loading arm 4 or the like. Further, the hardness testing apparatus 1 comprises a hardness calculating mechanism part 20 comprising an indentation depth sensor 8 for measuring a depth of an impression formed by the indentor 3, a hardness calculating unit 9 (shown in FIG. 3) for calculating a hardness of the sample S on the basis of measuring the depth by using the indentation depth sensor 8 or the like. The hardness testing apparatus 1 comprises a force inputting part for inputting a set force, which is not shown in the drawings.

The loading arm operating part 6, a control unit 21 which is a driving unit for the loading arm operating part 6 and the like are provided in the testing apparatus body 2. As shown in FIG. 1, a part of the loading arm operating part 6 is contained in the test apparatus body 2.

The loading arm 4 is supported by the testing apparatus body 2 so as to be movable rotationally by using a crossed spring 41, a rolling bearing or the like. The indentor 3 is attached to the free end of the loading arm 4 so as to be removal therefrom. Further, the loading arm 4 is united with the plate spring 7.

A notch 7a is provided between the plate spring 7 and the loading arm 4 in the longitudinal direction thereof. The end portion of the notch 7a is open.

The sample mounting member 5 has a square thread 51 attached to the bottom thereof. The sample mounting member 5 can move up and down with respect to the testing apparatus body 2 by the square thread 51. Further, the sample mounting member 51 has an automatic breaking mechanism 52.

The loading arm operating part 6 comprises a servo motor 61, a ball screw 62 and a fixture 63 which is attached to the end portion of the ball screw 62 and which is fixed to the plate spring 7. The loading arm operating part 6 is disposed below the arm 4. When the ball screw 62 moves up and down by driving the servo motor 61, the loading arm 4 united with the plate spring 7 is moved rotationally.

The fixture 63 for connecting the loading arm 4 with the loading arm operating part 6 has a function of correcting mis-alignment between an axis of the plate spring 7 and that of the loading arm operating part 6, which is caused by moving the loading arm 4 rotationally and by changing a form of the plate spring 7. For example, the fixture 63 has a structure in which a thin plate, a wire, such as a piano wire, or a knife edge is combined with a crossed spring, or in which only a universal joint or the like is used or a universal joint is used in combination with other members.

A spring displacement sensor 64 and a loading arm operation controlling unit 65, for controlling the operation of the loading arm 4, are attached to the loading arm 4 and to the plate spring 7. The spring displacement sensor 64 measures a displacement of the plate spring 7. When the displacement measured by the spring displacement sensor 64 is inputted into the loading arm operation controlling unit 65, the loading arm operation controlling unit 65 controls the operation of the ball screw 62 on the basis of the displacement.

For example, the spring displacement sensor 64 comprises a displacement sensor unit (linear scale) which reads a glass scale optically. The spring displacement sensor 64 measures a displacement of the plate spring 7 by moving down the ball screw 62 on the basis of an amount of an opening of the notch 7a between the plate spring 7 and the loading arm 4.

Figure 2:
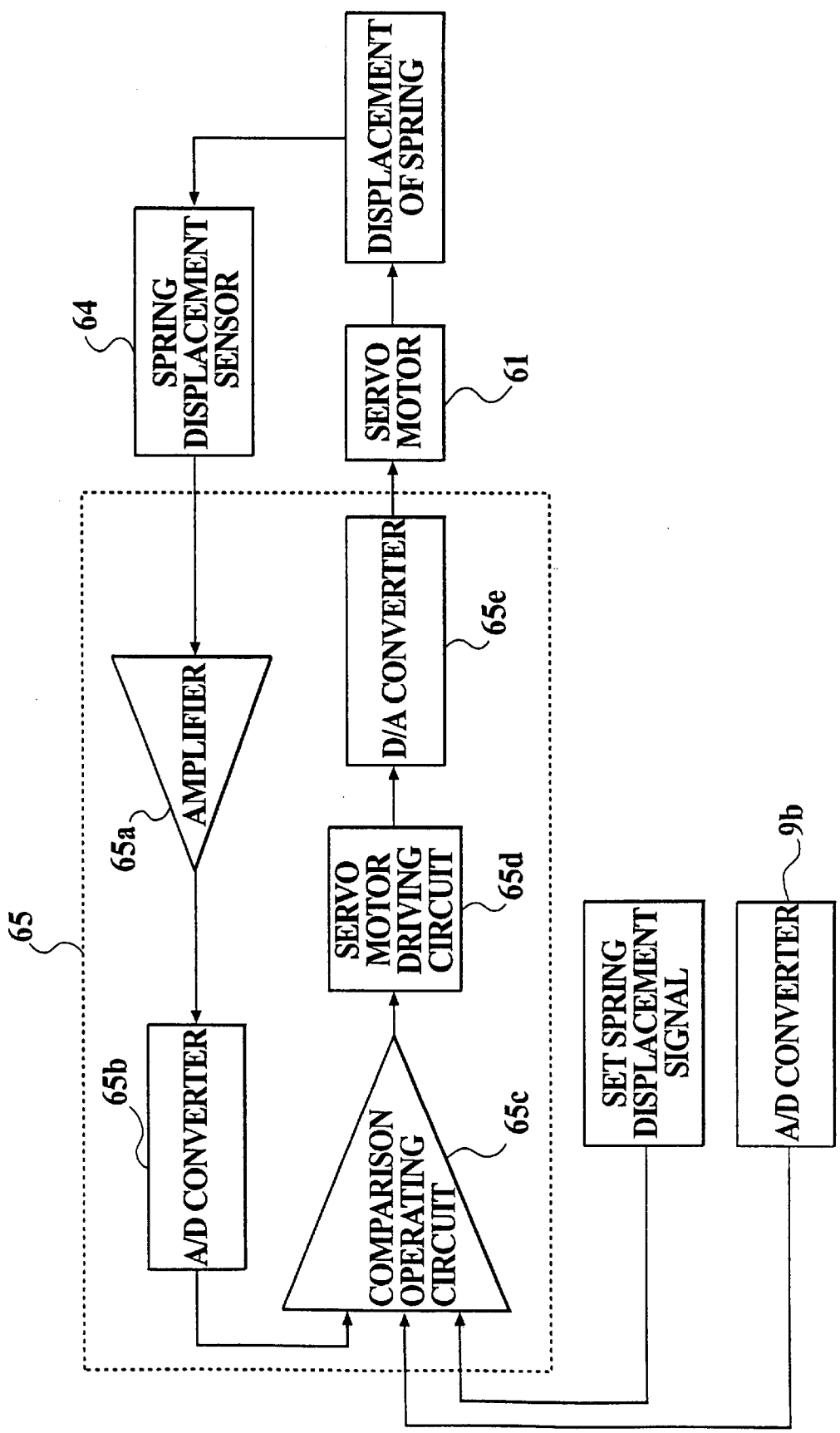
FIG. 2 is a block diagram showing a principal structure of a loading arm operation controlling unit according to the first embodiment of the present invention.

As shown in FIG. 2, the loading arm operation controlling unit 65 comprises an amplifier 65a, an A/D converter 65b, an comparison operating circuit 65c, a servo motor driving circuit 65d, a D/A converter 65e, or the like.

The amplifier 65a amplifies a spring displacement signal generated by measuring with the spring displacement sensor 64 in order to output it to the A/D converter 65b. The A/D converter 65b converts the amplified spring displacement signal from analog to digital, that is, the A/D converter 65b carries out the A/D conversion of the amplified spring displacement signal in order to output it to the comparison operating circuit 65c. The comparison operating circuit 65c compares the spring displacement signal converted from analog to digital with a set spring displacement signal (servo motor commanding data) which is previously set or with an indentation depth signal converted from analog to digital, which will be explained below. The comparison operating circuit 65c outputs the result of the above comparison to the servo motor driving circuit 65d.

The servo motor driving circuit 65d outputs a drive controlling signal for controlling the drive of the servo motor 61 so that the force to be applied to the sample S will become a set value on the basis of the result of the above comparison, to the D/A converter 65e. The D/A converter 65e converts the drive controlling signal from digital to analog in order to output to the servo motor 61.

The plate spring 7 transmits the force generated by the loading arm operating part 6 to the loading arm 4 as a rotating force. When the servo motor 61 drives electrically by inputting the drive controlling signal thereinto, the force generated by the servo motor 61 is applied to the plate spring 7. As a result, the free end side of the loading arm 4 moves rotationally.

The indentation depth sensor 8 comprises, for example, a displacement sensor unit (linear scale) which reads a glass scale optically, similarly to the spring displacement sensor 64. The indentation depth sensor 8 measures an amount of movement of the loading arm 4 in a vertical direction.

Figure 3:
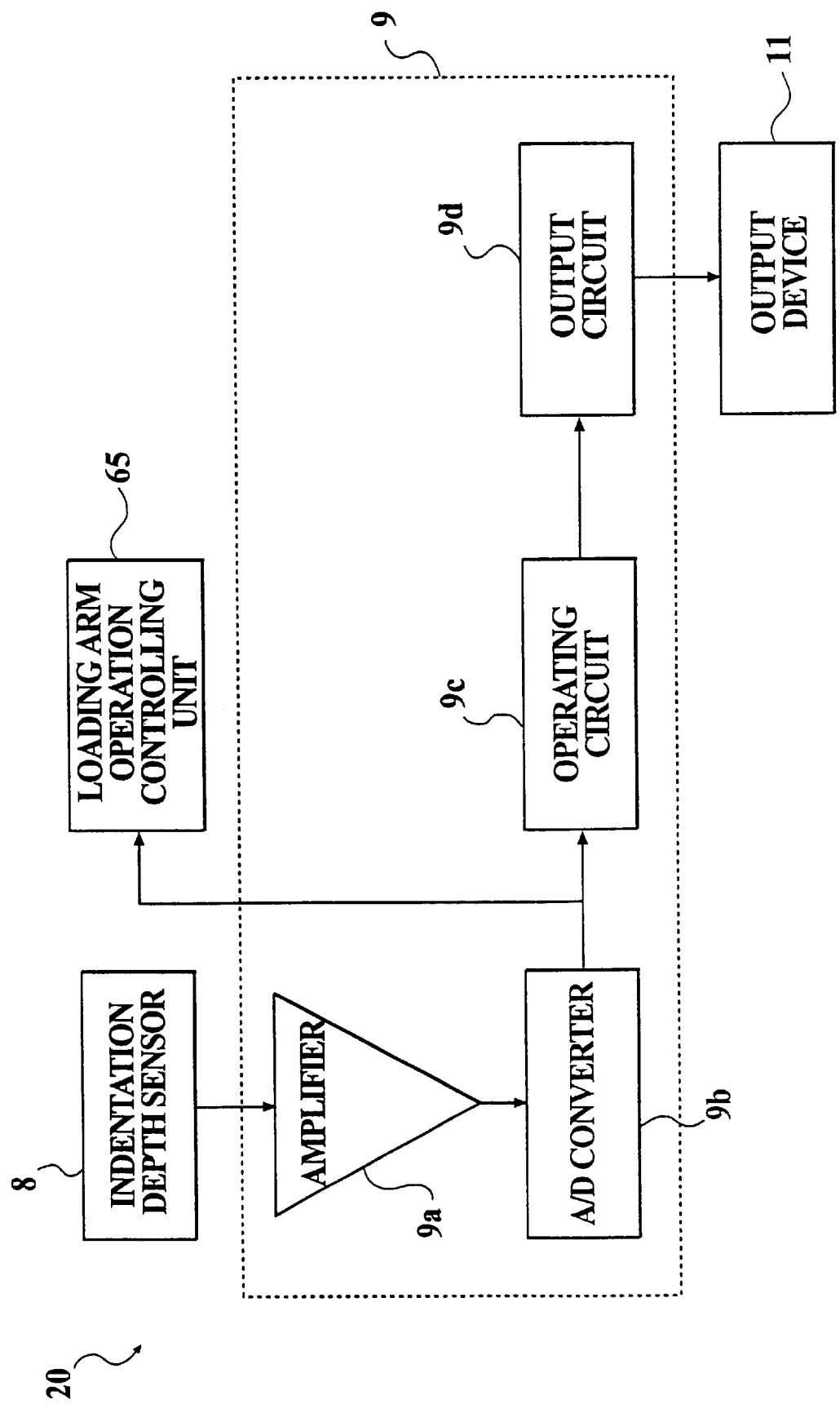
FIG. 3 is a block diagram showing a principal structure of a hardness calculating mechanism part according to the first embodiment of the present invention.

As shown in FIG. 3, the hardness calculating unit 9 comprises an amplifier 9a, an A/D converter 9b, an operating circuit 9c, an output circuit 9d and the like.

The amplifier 9a amplifies the indentation depth signal generated by measuring an amount of movement of the loading arm 4 with the indentation depth sensor 8 in order to output it to the A/D converter 9b. The A/D converter 9b converts the amplified indentation depth signal from analog to digital in order to output it to the operating circuit 9c.

The operating circuit 9c processes the indentation depth signal converted from analog to digital according to the operating program stored therein in order to calculate a hardness of the sample S. The operating circuit 9c outputs hardness data to the output circuit 9d. The output circuit 9d converts the hardness data outputted from the operating circuit 9c into data having a predetermined output form in order to output it to an output device 11 connected with the hardness testing apparatus 1. The output device 11 is, for example, a displaying device for displaying the hardness data or a printing device for printing out the hardness data.

Next, the operations of the hardness test carried out by using the above-described hardness testing apparatus will be explained below.

After the hardness testing apparatus 1 is switched on, the set force is inputted into the force inputting part which is not shown in the drawings. The set force signal generated by inputting the set force is outputted to the servo motor driving circuit 65d of the loading arm operation controlling unit 65.

When the drive controlling signal corresponding to the set force signal is outputted to the servo motor 61 by the servo motor driving circuit 65d, the servo motor 61 drives on the basis of the drive controlling signal. The ball screw 62 rotates by the drive of the servo motor 61 in order to move down. When the ball screw 62 moves down, the plate spring 7 fixed to the fixture 63 and the loading arm 4 united with the plate spring 7 are rotated downwardly around the crossed spring 41. The indentor 3 attached to the free end of the loading arm 4 contacts the sample S.

An amount of the opening of the notch 7a between plate spring 7 and the loading arm 4 is measured by the spring displacement sensor 64 in order to generate the spring displacement signal. The spring displacement signal is amplified in order to output it to the comparison operating circuit 65c through the A/D converter 65b.

The set spring displacement signal is compared with the spring displacement signal by the comparison operating circuit 65c in order to output the result of the comparison to the servo motor driving circuit 65d. The servo motor driving circuit 65d corrects the drive controlling signal on the basis of the result of the comparison so that the actual force to be applied to the indentor 3 will approximate to the set force. The corrected drive controlling signal is outputted to the servo motor 61. The servo motor 61 drives on the basis of the corrected drive controlling signal.

The above operations which are from the measurement carried out by the spring displacement sensor 64 to the correction of the drive controlling signal are repeatedly carried out in a closed loop. The drive control of the servo motor 61 is carried out. The force applied to the indentor 3 can maintain the value approximate to the set force during a predetermined time.

After the predetermined time passed, the depth of the impression is measured by the indentation depth sensor 8 in order to generate the indentation depth signal. The indentation depth signal is amplified by the amplifier 9a, is converted from analog to digital by the A/D converter 9b, and is outputted to the operating circuit 9c.

The indentation depth signal converted from analog to digital is processed according to the operating program stored in the operating circuit 9c in order to calculate the hardness of the sample S. The calculated hardness data are outputted to the predetermined output device 11 through the output circuit 9d.

As described above, in the impression forming mechanism according to the first embodiment of the present invention, because the loading arm operating part 6 for moving the loading arm 4 downwardly is disposed to the testing apparatus body 2 below the loading arm 4 and the indentor 3 is attached to the loading arm 4 directly, the structure of the parts disposed above the indentor 3 can be more simple than that of the mechanism according to the earlier development. The impression forming mechanism can make a testing apparatus be small in a height direction by attaching the impression forming mechanism to a hardness testing apparatus.

Because a part of the loading arm operating part 6 is contained in the testing apparatus body 2, the impression forming mechanism can be small.

In particular, the force generated by the loading arm operating part 6 can be transmitted to the loading arm 4 as a rotating force by the plate spring 7 completely.

Because the servo motor 61 applies the rotating force to the loading arm 4, the rotational movement of the loading arm 4 can be controlled more precisely than the movement of the arm, which is carried out by weights and cam mechanism according to the earlier development.

Further, because the loading arm 4 is used and the force control is carried out on the basis of the displacement of the plate spring 7, it is not necessary that the compensating control which must be carried out when the force control is carried out by using the load cell because of the structural defect of the load cell, in which an amount of an indentation (that is, a hardness of a sample) includes an amount of a strain of the load cell, is carried out. As a result, an amount of an indentation of the indentor can be measured precisely. The above method is effective, in particular when an amount of an indentation of the indentor is measured dynamically and a hardness of a sample is calculated.

In the above-described first embodiment, although a linear scale is used in the spring displacement sensor 64 and the indentation depth sensor 8, the present invention is not limited to this. For example, a capacitance displacement transducer may be used as a spring displacement sensor. Further, an LVDT (a linear variable differential transformer), an electric micrometer or the like may be used as an indentation depth sensor.

Although the output device 11 is separated from the hardness testing apparatus 1, the output device 11 may be incorporated into the hardness testing apparatus 1.

Next, an impression forming mechanism and a hardness testing apparatus according to the second embodiment of the present invention will be explained in detail with reference to the FIGS. 4 to 6.

Figure 4:
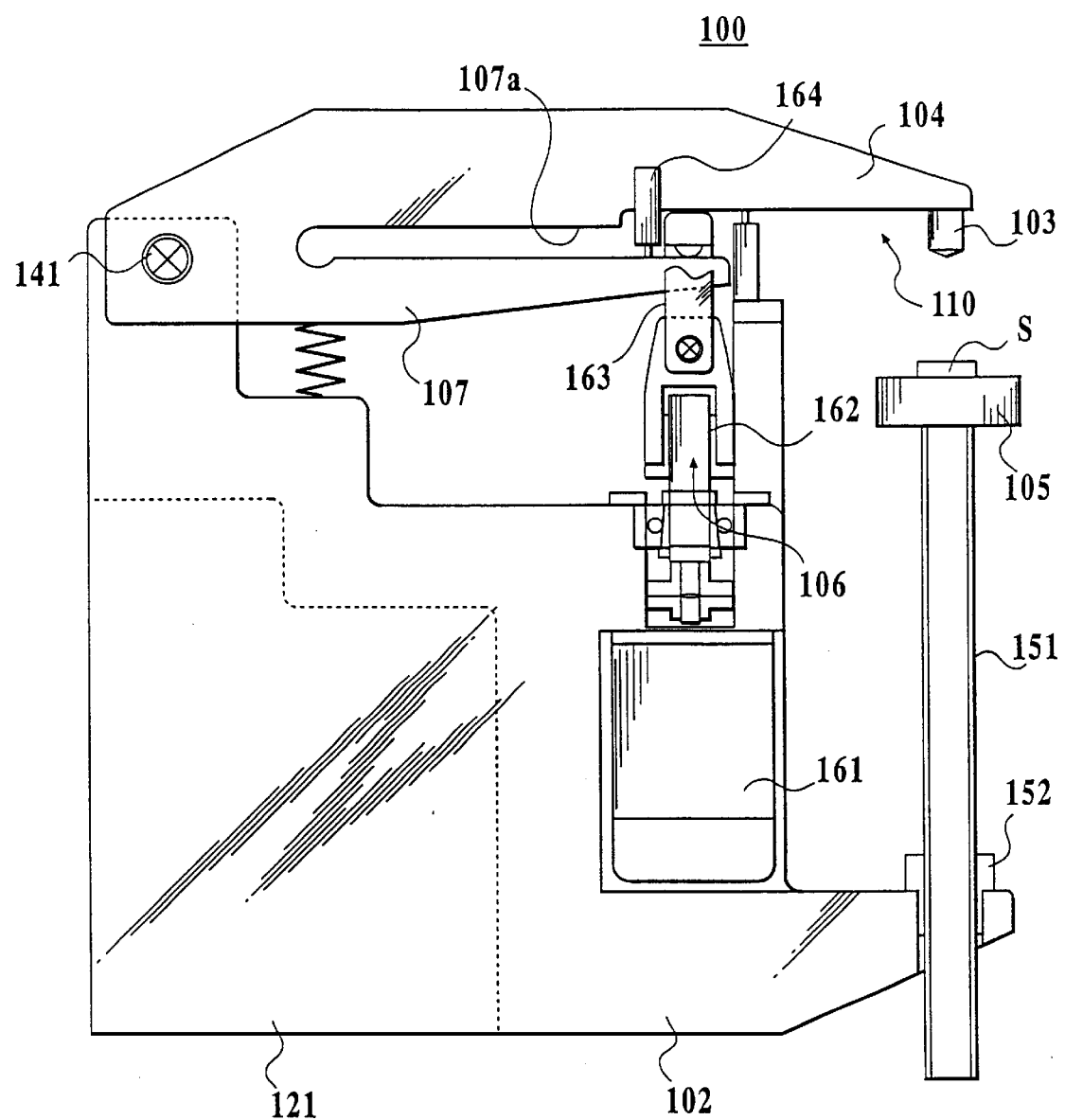
FIG. 4 is a side view showing a principal structure of a hardness testing apparatus according to the second embodiment of the present invention.

FIG. 4 is a side view showing a principal structure of a hardness testing apparatus according to the second embodiment of the present invention. FIG. 5 is a block diagram showing a principal structure of a loading arm operation controlling unit according to the second embodiment of the present invention. FIG. 6 is a block diagram showing a principal structure of a hardness calculating mechanism part according to the second embodiment of the present invention.

The hardness testing apparatus 100 shown in FIG. 4 comprises an impression forming mechanism 110 comprising a testing apparatus body 102, a loading arm 104 which is supported by the testing apparatus body 102 so as to be movable rotationally and which has an indentor 103 attached to the free end thereof, a sample mounting member 105 for mounting a sample S, which is attached to the testing apparatus body 102 below the indentor 103, a loading arm operating part 106 arranged below the loading arm 104, which applies force (load) for pressing a surface of the sample S in order to form an impression thereon by moving the free end side of the loading arm 104 rotationally, a plate spring 107 for transmitting force generated by operating the loading arm operating part 106 to the loading arm 104 or the like. Further, the hardness testing apparatus 100 comprises a hardness calculating mechanism part 120 comprising an indentation depth sensor 108 for measuring a depth of an impression formed by the indentor 103, a hardness calculating unit 109 (shown in FIG. 6) for calculating a hardness of the sample S on the basis of measuring the depth by using the indentation depth sensor 108 or the like. The hardness testing apparatus 100 comprises a force inputting part 130 (shown in FIG. 5) for inputting a set force.

The loading arm operating part 106, a control unit 121 which is a driving unit for the loading arm operating part 106 and the like are provided in the testing apparatus body 102. The loading arm 104 is supported by the testing apparatus body 102 so as to be movable rotationally by using a crossed spring 141, a rolling bearing or the like. The indentor 103 is attached to the free end of the loading arm 104 so as to be removal therefrom. Further, the loading arm 104 is united with the plate spring 107.

A notch 107a is provided between the plate spring 107 and the loading arm 104 in the longitudinal direction thereof. The end of the notch 107a is open on the indentor 103 side.

The sample mounting member 105 has a square thread 151 attached to the bottom thereof. The sample mounting member 105 can move up and down with respect to the testing apparatus body 102 by the square thread 151. Further, the sample mounting member 151 has an automatic breaking mechanism 152.

The loading arm operating part 106 comprises a servo motor 161, a ball screw 162 and a fixture 163 which is attached to the end portion of the ball screw 162 and which is fixed to the plate spring 107. When the ball screw 162 moves up and down by driving the servo motor 161, the loading arm 104 united with the plate spring 107 is moved rotationally.

The fixture 163 for connecting the loading arm 104 with the loading arm operating part 106 has a function of correcting mis-alignment between an axis of the plate spring 107 and that of the loading arm operating part 106, which is caused by moving the loading arm 104 rotationally and by changing a form of the plate spring 107. For example, the fixture 163 has a structure in which a thin plate, a wire, such as a piano wire, or a knife edge is combined with a crossed spring, or in which only a universal joint or the like is used or a universal joint is used in combination with other members.

A spring displacement sensor 164 and a loading arm operation controlling unit 165, for controlling the operation of the loading arm 104, are attached to the loading arm 104 and to the plate spring 107. The spring displacement sensor 164 measures an amount of a deformation (a displacement) of the plate spring 107. When the amount of the deformation, which is measured by the spring displacement sensor 164 is inputted into the loading arm operation controlling unit 165, the loading arm operation controlling unit 165 controls the operation of the ball screw 162 on the basis of the amount of the deformation of the plate spring 107.

For example, the spring displacement sensor 164 comprises a displacement sensor unit (linear scale) which reads a glass scale optically. The spring displacement sensor 164 measures an amount of the deformation of the plate spring 107 by moving down the ball screw 162 on the basis of an amount of an opening of the notch 107a between the plate spring 107 and the loading arm 104.

Figure 5:
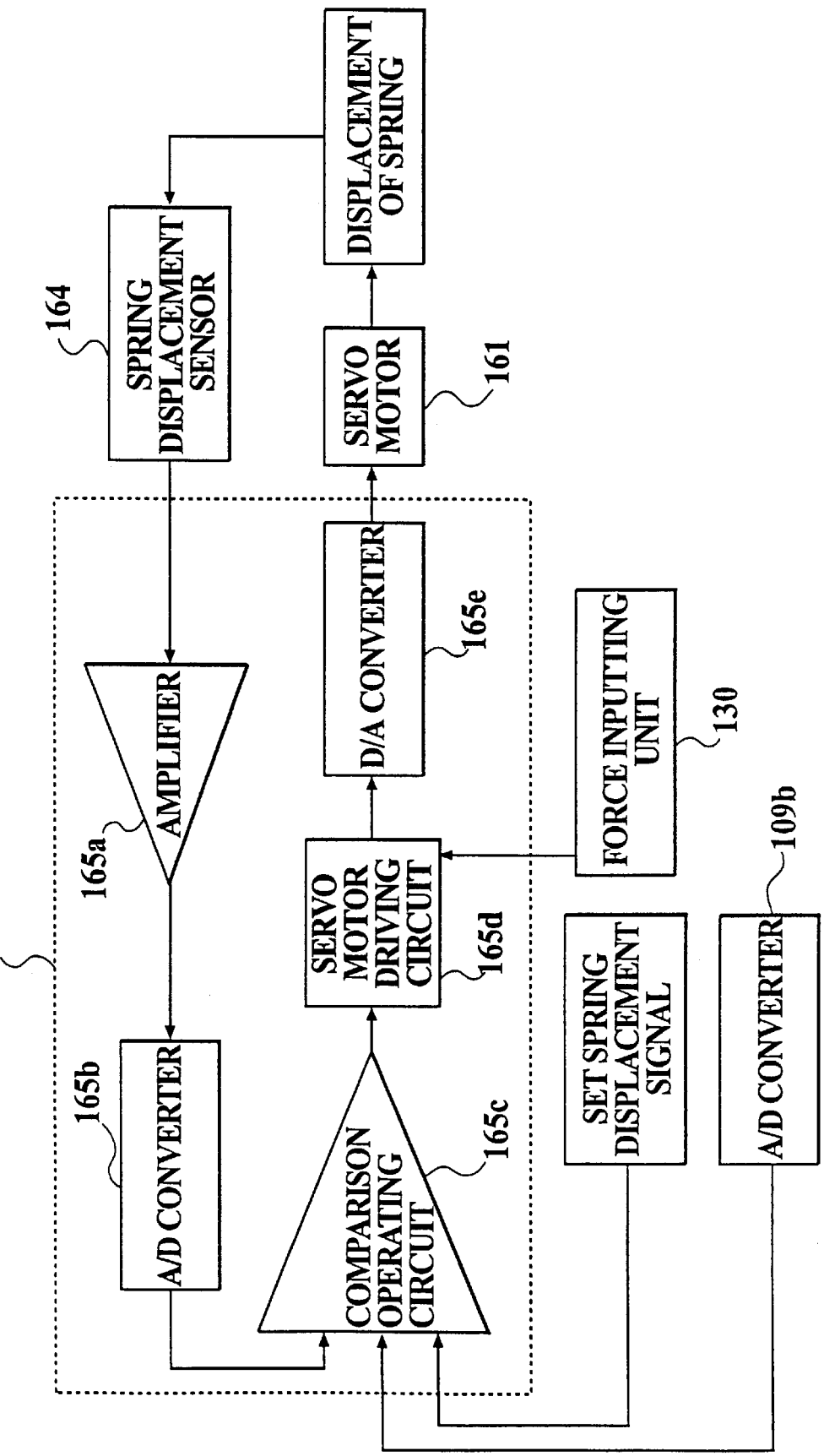
FIG. 5 is a block diagram showing a principal structure of a loading arm operation controlling unit according to the second embodiment of the present invention.

As shown in FIG. 5, the loading arm operation controlling unit 165 comprises an amplifier 165a, an A/D converter 165b, an comparison operating circuit 165c, a servo motor driving circuit 165d, a D/A converter 165e, or the like.

The amplifier 165a amplifies a spring displacement signal generated by measuring with the spring displacement sensor 164 in order to output it to the A/D converter 165b. The A/D converter 165b converts the amplified spring displacement signal from analog to digital, that is, the A/D converter 165b carries out the A/D conversion of the amplified spring displacement signal in order to output it to the comparison operating circuit 165c. The comparison operating circuit 165c compares the spring displacement signal converted from analog to digital with a set spring displacement signal (servo motor commanding data) which is previously set. The comparison operating circuit 165c outputs the result of the above comparison to the servo motor driving circuit 165d.

The servo motor driving circuit 165d outputs a drive controlling signal for controlling the drive of the servo motor 161 so that the force to be applied to the sample S will become a set value on the basis of the result of the above comparison, to the D/A converter 165e. The D/A converter 165e converts the drive controlling signal from digital to analog in order to output to the servo motor 161.

The plate spring 107 transmits the force generated by the loading arm operating part 106 to the indentor 103 through the loading arm 104. When the servo motor 161 drives electrically by inputting the drive controlling signal thereinto, the force generated by the servo motor 161 is applied to the plate spring 107. The plate spring 107 is deformed elastically by the force applied thereto in order to store the force for forming the impression on the surface of the sample S.

The indentation depth sensor 108 comprises, for example, a displacement sensor unit (linear scale) which reads a glass scale optically, similarly to the spring displacement sensor 164. The indentation depth sensor 108 measures an amount of movement of the loading arm 104 in a vertical direction.

Figure 6:
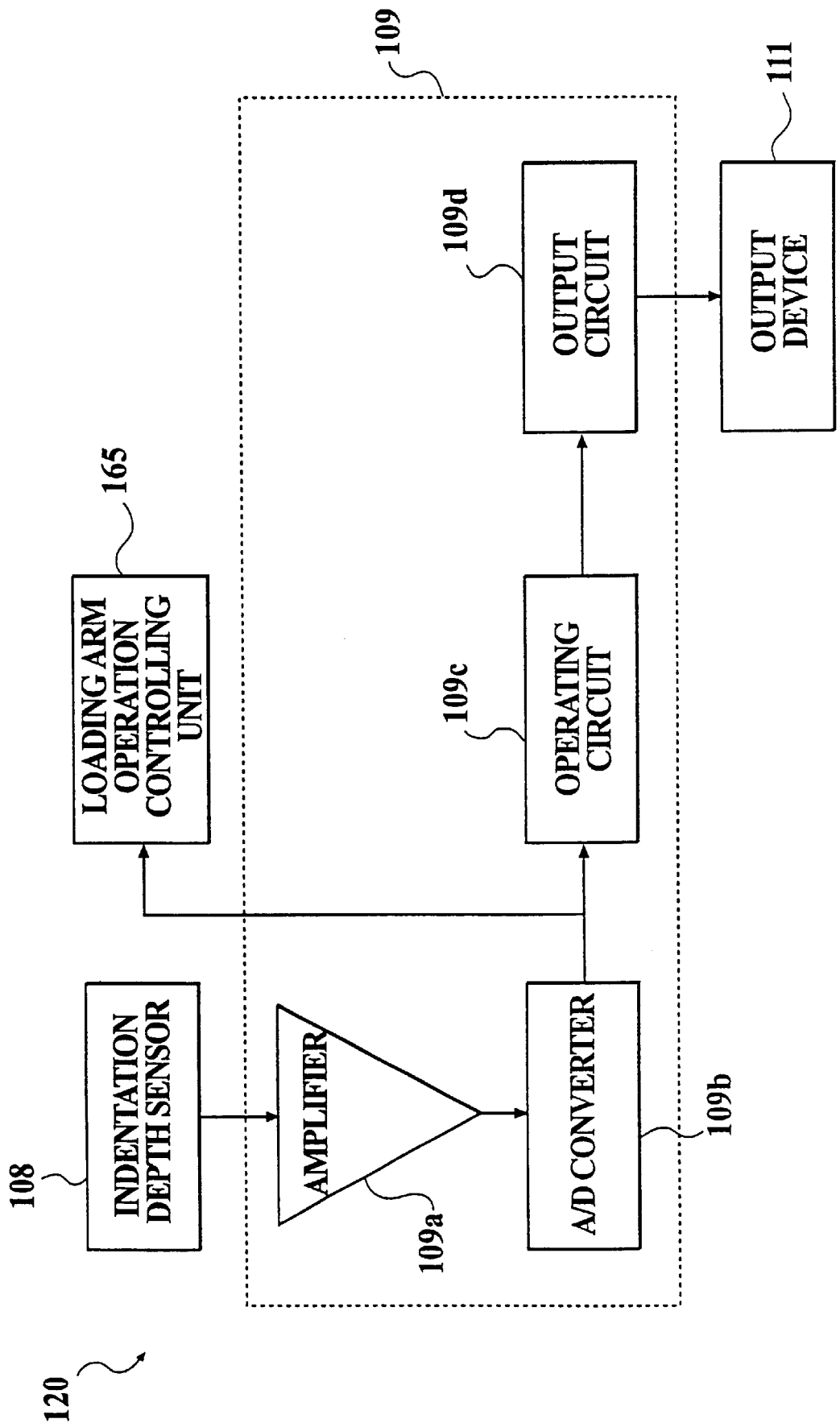
FIG. 6 is a block diagram showing a principal structure of a hardness calculating mechanism part according to the second embodiment of the present invention.
Figure 7:
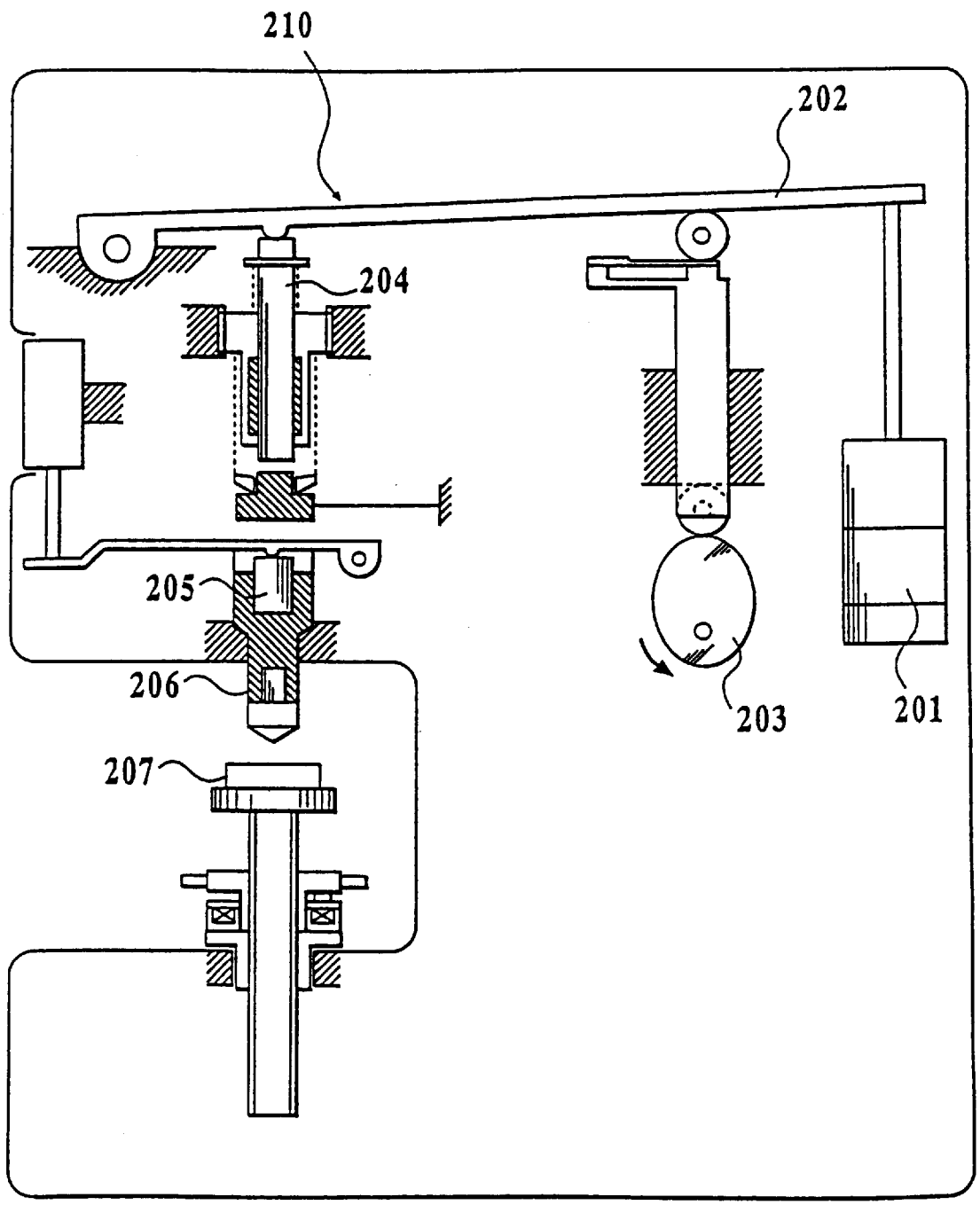
FIG. 7 is a side view showing a principal structure of a hardness testing apparatus according to an earlier development.

As shown in FIG. 6, the hardness calculating unit 109 comprises an amplifier 109a, an A/D converter 109b, an operating circuit 109c, an output circuit 109d and the like.

The amplifier 109a amplifies the indentation depth signal generated by measuring an amount of movement of the loading arm 104 with the indentation depth sensor 108 in order to output it to the A/D converter 109b. The A/D converter 109b converts the amplified indentation depth signal from analog to digital in order to output it to the operating circuit 109c.

The operating circuit 109c processes the indentation depth signal converted from analog to digital according to the operating program stored therein in order to calculate a hardness of the sample S. The operating circuit 109c outputs hardness data to the output circuit 109d. The output circuit 109d converts the hardness data outputted from the operating circuit 109c into data having a predetermined output form in order to output it to an output device 111 connected with the hardness testing apparatus 100. The output device 111 is, for example, a displaying device f or displaying the hardness data or a printing device for printing out the hardness data.

Next, the operations of the hardness test carried out by using the above-described hardness testing apparatus will be explained below.

After the hardness testing apparatus 100 is switched on, the set force is inputted into the force inputting part 130. The set force signal generated by inputting the set force is outputted to the servo motor driving circuit 165d of the loading arm operation controlling unit 165.

When the drive controlling signal corresponding to the set force signal is outputted to the servo motor 161 by the servo motor driving circuit 165d, the servo motor 161 drives on the basis of the drive controlling signal. The ball screw 162 rotates by the drive of the servo motor 161 in order to move down. When the ball screw 162 moves down, the plate spring 107 fixed to the fixture 163 and the loading arm 104 united with the plate spring 107 are rotated downwardly around the crossed spring 141. The indentor 103 attached to the free end of the loading arm 104 contacts the sample S.

An amount of the opening of the notch 107a between plate spring 107 and the loading arm 104 is measured by the spring displacement sensor 164 in order to generate the spring displacement signal. The spring displacement signal is amplified in order to output it to the comparison operating circuit 165*c* through the A/D converter 165*b*.

The set spring displacement signal is compared with the spring displacement signal by the comparison operating circuit 165*c* in order to output the result of the comparison to the servo motor driving circuit 165*d*. The servo motor driving circuit 165*d* corrects the drive controlling signal on the basis of the result of the comparison so that the actual force to be applied to the indentor 103 will approximate to the set force. The corrected drive controlling signal is outputted to the servo motor 161. The servo motor 161 drives on the basis of the corrected drive controlling signal.

The above operations which are from the measurement carried out by the spring displacement sensor 164 to the correction of the drive controlling signal are repeatedly carried out in a closed loop. The drive control of the servo motor 161 is carried out. The force applied to the indentor 103 can maintain the value approximate to the set force during a predetermined time.

After the predetermined time passed, the depth of the impression is measured by the indentation depth sensor 108 in order to generate the indentation depth signal. The indentation depth signal is amplified by the amplifier 109*a*, is converted from analog to digital by the A/D converter 109*b*, and is outputted to the operating circuit 109*c*.

The indentation depth signal converted from analog to digital is processed according to the operating program stored in the operating circuit 109*c* in order to calculate the hardness of the sample S. The calculated hardness data are outputted to the predetermined output device 111 through the output circuit 109*d*.

As described above, in the impression forming mechanism 110 and the hardness testing apparatus 100 according to the second embodiment of the present invention, the force generated by the loading arm operating part 106 is transmitted to the indentor 103 through the loading arm 104. At the same time, the plate spring 107 is deformed elastically. An amount of an elastic deformation of the plate spring 107 is measured by the spring displacement sensor 164 by setting the predetermined reference position of the predetermined part thereof to a reference point. The amount of the measured elastic deformation is compared with a reference amount of the elastic deformation, which is previously set, by the loading arm operation controlling unit 165. Because the control of applying the force by the loading arm operating part 106 is carried out on the basis of the result of the above comparison, it is possible not only that the force for forming the impression becomes the set value approximately but also that the force applying control is carried out without the load cell. As a result, the force applying control can be carried out cheaper. In particular, because the force applying control is carried out by the loading arm operation controlling unit 165 in a closed loop, the force applying control is always carried out. As a result, the force for forming the impression can become the set force more approximately.

Because the plate spring 107 and the spring displacement sensor 164 can obtain the effect which is the same as the load cell, not only the force control can be carried out precisely but also the impression forming mechanism is manufactured cheaper.

In the above-described second embodiment, although a linear scale is used in the spring displacement sensor 164 and the indentation depth sensor 108, the present invention is not limited to this. For example, a capacitance displacement transducer may be used as a spring displacement sensor. Further, an LVDT (a linear variable differential transformer), an electric micrometer or the like may be used as an indentation depth sensor.

Although the plate spring 107 is illustrated in the second embodiment, a spring may be used other than the plate spring. An elastic body, for example, a rubber, may be used.

According to the present invention, because the arm rotating force applying part for moving the free end side of the arm rotationally is disposed to the body part below the arm and the indentor is attached to the arm directly, the structure of the parts disposed above the indentor can be more simple than that of the mechanism in which the arm is disposed apart from the indentor and in which a part for operating the arm is disposed between them, according to the earlier development. The impression forming mechanism can make a testing apparatus be small in a height direction by attaching the impression forming mechanism to a hardness testing apparatus.

In particular, the force generated by the arm rotating force applying part can be transmitted to the arm as a rotating force by the rotating force transmitting member completely.

Because a part of the arm rotating force applying part is contained in the body part, the impression forming mechanism can be small.

Because the electric operating member applies the rotating force to the arm, the rotational movement of the arm can be controlled more precisely than the movement of the arm, which is carried out by weights and cam mechanism according to the earlier development.

The hardness testing apparatus can be small by applying the impression forming mechanism according to the present invention.

According to the present invention, the force applied by the force applying part is transmitted to the indentor by the force transmitting member. At the same time, the force transmitting member is deformed elastically by the force. An amount of an elastic deformation of the force transmitting member is measured by the deformation measuring unit by setting the predetermined reference position of the predetermined part thereof to a reference point. Because the control of applying the force by the force applying part is carried out by the force applying control unit on the basis of the amount of the measured elastic deformation, it is possible not only that the force (load) for forming the impression becomes the set value approximately but also that the force applying control is carried out without the load cell. As a result, the force applying control can be carried out cheaper.

Further, because the loading arm is used and the force control is carried out on the basis of the displacement of the force transmitting member, it is not necessary that the compensating control which must be carried out when the force control is carried out by using the load cell because of the structural defect of the load cell, in which an amount of an indentation (that is, a hardness of a sample) includes an amount of a strain of the load cell, is carried out. As a result, an amount of an indentation of the indentor can be measured precisely. The above method is effective, in particular when an amount of an indentation of the indentor is measured dynamically and a hardness of a sample is calculated.

In particular, because the control of the force applied by the force applying part is carried out in a closed loop, the force applying control is always carried out. As a result, the force for forming the impression can become the set force more approximately.

Because the force transmitting member is a spring body, the spring body and the deformation measuring unit can obtain the effect which is the same as the load cell. As a result, the force control can be carried out precisely. The impression forming mechanism is manufactured cheaper.

It is possible to provide the precise and cheap hardness testing apparatus by comprising the impression forming mechanism according to the present invention.

The entire disclosures of Japanese Patent Application Nos. Tokugan-Hei 11-38913 and 11-38914 filed on Feb. 17, 1999 including specification, claims drawings and summary are incorporated herein by reference in its entirety.

What is claimed is:

1. An impression forming mechanism which is used for a testing apparatus for measuring material characteristics of a sample by forming an impression with an indentor on a surface of the sample, comprising:

a body part, an arm member having an arm portion and an elastic body portion, the arm portion being supported by the body part so as to be movable rotationally and attaching the indentor to a free end portion thereof, and the elastic body portion being elastically deformed so as to store a pressing force for forming the impression on the surface of the sample, an arm rotating force applying part for applying a force to the arm portion in order to move a free end side of the arm portion rotationally and in order to apply the pressing force by deforming the elastic body portion, a deformation measuring member for measuring an amount of a deformation of the elastic body portion, and a force control unit for controlling the pressing force stored in the elastic body portion on the basis of the amount of the deformation of the elastic body portion, which is measured by the deformation measuring member, wherein the arm rotating force applying part is attached to the body part below the arm portion.

2. The impression forming mechanism as claimed in claim 1, wherein the force control unit comprises a closed loop system for controlling the pressing force stored in the elastic body portion in a closed loop.

3. The impression forming mechanism as claimed in claim 1, wherein the arm rotating force applying part pulls the arm portion via the elastic body portion when the pressing force is applied to the indentor.

4. The impression forming mechanism as claimed in claim 3, wherein the elastic body portion is a plate spring, and the arm portion is united with the plate spring.

5. The impression forming mechanism as claimed in claim 1, wherein the deformation measuring member comprises a linear scale.

6. The impression forming mechanism as claimed in claim 1, wherein the elastic body portion transmits the force generated by the arm rotating force applying part to the arm portion as a rotating force.

7. The impression forming mechanism as claimed in claim 1, wherein a part of the arm rotating force applying part is within the body part.

8. The impression forming mechanism as claimed in claim 1, further comprising an electric operating member, wherein the arm rotating force applying part applies a rotating force to the arm portion by operating the electric operating member.

9. A hardness testing apparatus comprising:

a body part, an arm member having an arm portion and an elastic body portion, the arm portion being supported by the body part so as to be movable rotationally and attaching an indentor to a free end portion thereof, and the elastic body portion being elastically deformed so as to store a pressing force for forming the impression on the surface of the sample, an arm rotating force applying part for applying a force to the arm portion in order to move a free end side of the arm portion rotationally and in order to apply the pressing force by deforming the elastic body portion a hardness calculating mechanism part for measuring a shape of the impression formed on the surface of the sample, and for calculating a hardness of the sample on the basis of a result of measuring the shape of the impression, a deformation measuring member for measuring an amount of a deformation of the elastic body portion, and a force control unit for controlling the pressing force stored in the elastic body portion on the basis of the amount of the deformation of the elastic body portion, which is measured by the deformation measuring member, wherein the arm rotating force applying part is attached to the body part below the arm portion.

10. The hardness testing apparatus as claimed in claim 9, wherein the force control unit comprises a closed loop system for controlling the pressing force stored in the elastic body portion in a closed loop.

11. The hardness testing apparatus as claimed in claim 9, wherein the arm rotating force applying part pulls the arm portion via the elastic body portion when the pressing force is applied to the indentor.

12. The hardness testing apparatus as claimed in claim 11, wherein the elastic body portion is a plate spring, and the arm portion is united with the plate spring.

13. The hardness testing apparatus as claimed in claim 9, wherein the deformation measuring unit comprises a linear scale.

14. The hardness testing apparatus as claimed in claim 9, wherein the elastic body portion transmits the force generated by the arm rotating force applying part to the arm portion as a rotating force.

15. The hardness testing apparatus as claimed in claim 9, wherein a part of the arm rotating force applying part is within the body part.

16. The hardness testing apparatus as claimed in claim 9, further comprising an electric operating member, wherein the arm rotating force applying part applies a rotating force to the arm portion by operating the electric operating member.

* * * * *